(12) United States Patent
Peltier

(10) Patent No.: US 7,871,574 B2
(45) Date of Patent: Jan. 18, 2011

(54) FLASK FOR PREPARING A CYTOLOGICAL SUSPENSION

(75) Inventor: Eric Peltier, Clamart (FR)

(73) Assignee: Maclip, Clamart (FR)

( * ) Notice: Subject to any disclaimer, the term of this patent is extended or adjusted under 35 U.S.C. 154(b) by 572 days.

(21) Appl. No.: 11/791,821

(22) PCT Filed: Nov. 28, 2005

(86) PCT No.: PCT/FR2005/002953

§ 371 (c)(1),
(2), (4) Date: Jun. 25, 2007

(87) PCT Pub. No.: WO2006/058989

PCT Pub. Date: Jun. 8, 2006

(65) Prior Publication Data

US 2008/0070295 A1    Mar. 20, 2008

(30) Foreign Application Priority Data

Nov. 30, 2004    (FR) .................................. 04 12710

(51) Int. Cl.
| | |
|---|---|
| *B01L 3/00* | (2006.01) |
| *A61B 10/00* | (2006.01) |
| *C12M 1/36* | (2006.01) |
| *C12M 1/38* | (2006.01) |
| *C12M 3/00* | (2006.01) |
| *C12M 1/12* | (2006.01) |
| *C12M 1/00* | (2006.01) |

(52) U.S. Cl. .................... 422/102; 600/569; 435/286.7; 435/297.1; 435/307.1

(58) Field of Classification Search ................. 422/102; 435/307.1

See application file for complete search history.

(56) References Cited

U.S. PATENT DOCUMENTS

| | | | | |
|---|---|---|---|---|
| 4,657,869 | A | * | 4/1987 | Richards et al. .......... 435/287.6 |
| 5,422,273 | A | * | 6/1995 | Garrison et al. .......... 435/307.1 |
| 5,817,032 | A | * | 10/1998 | Williamson et al. ......... 600/562 |
| 6,063,038 | A |   | 5/2000 | Diamond et al. |
| 6,346,087 | B1 | * | 2/2002 | Peltier ........................ 600/569 |
| 2005/0109689 | A1 | * | 5/2005 | Trachtenbroit .............. 210/238 |

FOREIGN PATENT DOCUMENTS

EP    1 044 652    10/2000

\* cited by examiner

*Primary Examiner*—Sam Siefke
*Assistant Examiner*—Bryan T Kilpatrick
(74) *Attorney, Agent, or Firm*—Young & Thompson

(57) ABSTRACT

A flask for preparing a fixer-based cytological suspension is equipped with a filtering element (4) at least partly immersed in the suspension. The filtering element is in the form of a basket-forming filtering material web, whereof the periphery (5) is fixed on the flask and whereof the center (6) is connected to a tube (7), extending towards the opening (2) of the flask, associated with a position-maintaining element (8) in the flask and adapted to allow through a pipette for drawing the suspension.

15 Claims, 2 Drawing Sheets

FLASK FOR PREPARING A CYTOLOGICAL SUSPENSION

BACKGROUND OF THE INVENTION

1. Field of the Invention

Figure 1:
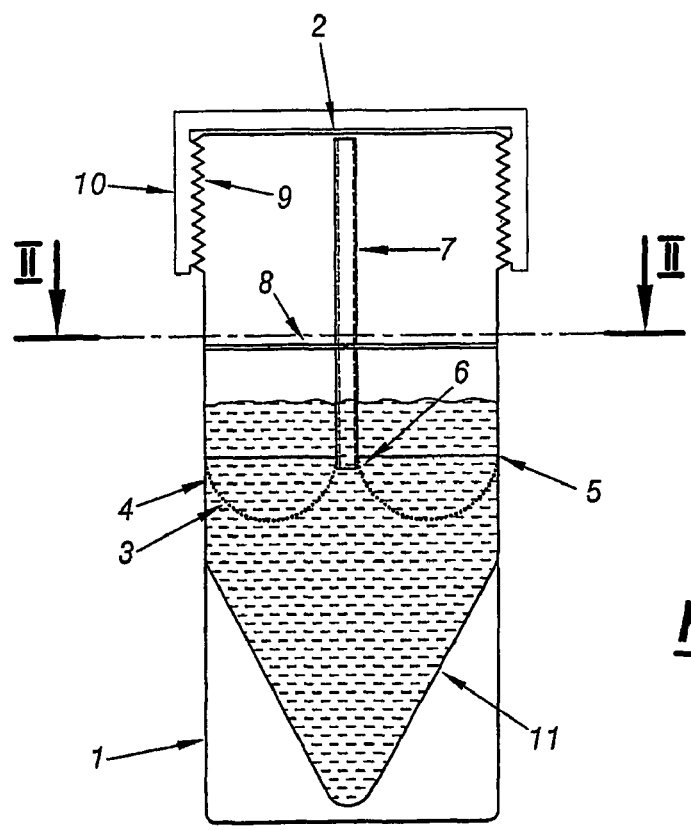

The present invention relates to a flask for preparing a fixer-based cytological suspension.

2. Description of the Related Art

Flasks of this type are used in the state of the art for preparing cytological suspensions, particularly cervical or vaginal cytological suspensions, for analysis, etc . . .

Samples, particularly cervical or vaginal samples, are taken by practitioners with the aid of special brushes which are fixed, for example releasably, to manipulating handles.

Once the sample has been taken, the practitioner plunges the brush into the flask and detaches it from the handle so as to allow the sampled cells to be deposited in the fixer.

However, undesirable components may also be deposited in the fixer such as, for example, debris picked up by the brush during the sampling (mucous, aggregations, etc. . . .), or skin scales from the practitioner that are deposited in the flask, particularly during handling of the brush in order to detach it from the handle, etc.

These components may be very inconvenient during subsequent analysis of the suspension.

The Applicant has already proposed a particular flask structure to try to solve these problems.

That flask is described in the document FR-A-2 792 331.

According to that document, the flask has an opening for receiving a cytological sampling brush fixed releasably to a manipulating handle and is characterized in that the opening of the flask comprises abutment means for the brush, enabling the brush to be trapped in the flask and detached from the handle, and at least one portion of perforated web for filtering the suspension during a pouring operation.

However, in use, a flask of this type has also shown some disadvantages particularly with regard to clogging of the portion of perforated suspension-filtering web by the above mentioned components.

SUMMARY OF THE INVENTION

The object of the invention is therefore further to improve these preparation flasks.

For this purpose, the subject of the invention is a flask for preparing a fixer-based cytological suspension, equipped with filtering means at least partially immersed in the suspension, characterized in that the filtering means are in the form of a web of filtering material forming a strainer, whereof the periphery is fixed to the flask and whereof the centre is connected to a tube that extends towards the opening of the flask, is associated with means for holding it in position in the flask, and is adapted to allow through a pipette for extracting the suspension.

According to further characteristics of the invention:
the upper part of the flask is adapted to receive a cover,
the cover and the corresponding part of the flask comprise complementary screwing means,
the cover comprises, facing the corresponding end of the tube, at least one piercable and self-sealing portion through which the extraction pipette can pass and which is adapted to come to bear against that end of the tube in order to ensure leaktightness between the tube and the remainder of the flask,
the lower part of the flask comprises means forming a decantation cone,
the means for holding the tube in the flask comprise position-maintaining arms extending between the flask and the tube,
one of the arms comprises abutment means for enabling a sampling brush to be detached from a manipulating handle in order for the brush to fall into the strainer, and
one of the arms comprises barbs for combing a sampling brush in order to cause the elements sampled thereby to fall into the strainer.

BRIEF DESCRIPTION OF THE DRAWING FIGURES

Figure 2:
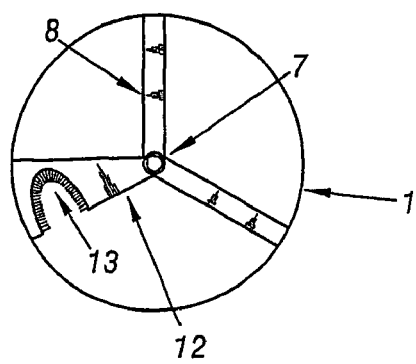
Figure 3:
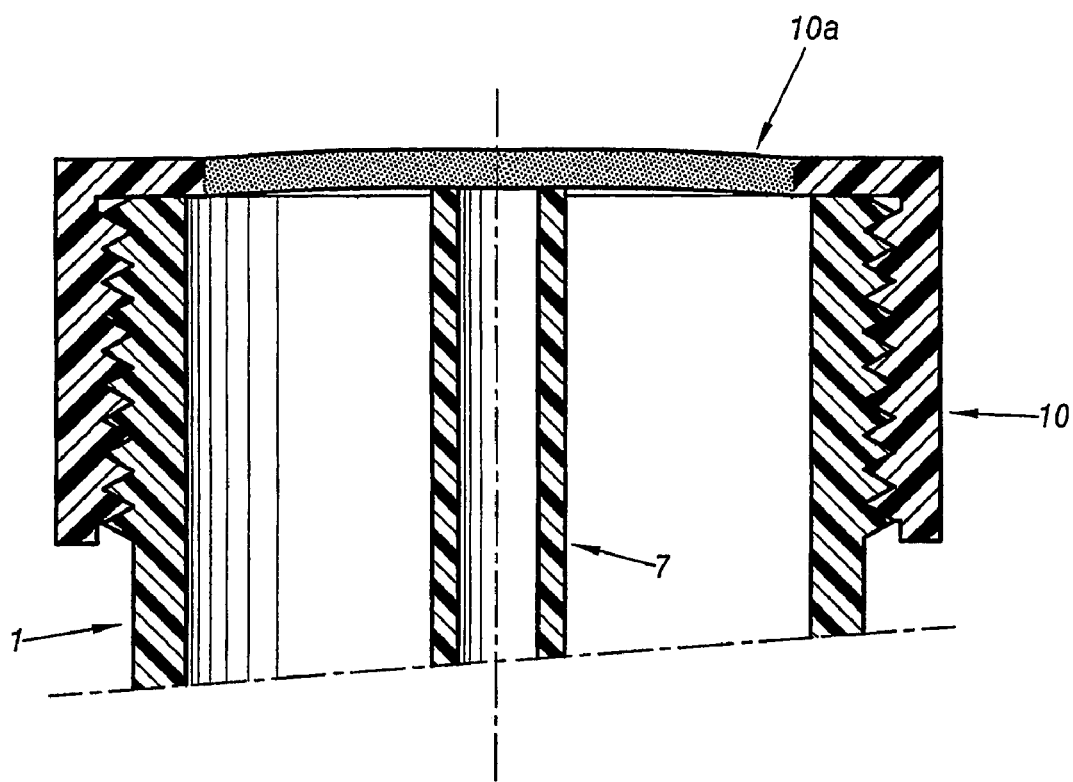

The invention will be understood further from a reading of the following description which is given purely by way of example with reference to the appended drawings in which:

FIG. 1 is a sectioned, schematic side view of a preparation flask according to the invention, FIG. 2 is a partial schematic view of such a flask from above, and FIG. 3 is a partial, sectioned, schematic side view of a portion of a preparation flask according to the invention.

DETAILED DESCRIPTION

An embodiment of the flask according to the invention is in fact illustrated in FIGS. 1 and 2.

The flask is a flask for preparing a fixer-based cytological suspension.

The flask is generally indicated 1 and comprises an opening, generally indicated 2, through which a cytological sampling brush can pass.

The flask is equipped with filtering means at least partially immersed in the suspension.

The filtering means are generally indicated 3 in this drawing and, according to the invention, take the form of a web of filtering material forming a strainer, generally indicated 4, the periphery 5 of which is fixed to the flask and the centre 6 of which is connected to a tube 7 that extends towards the opening 2 of the flask, is associated with means, generally indicated 8, for holding it in position, for example in a central position, in the flask, and is adapted to allow through a pipette for extracting the suspension.

The upper part of the flask, generally indicated 9 in FIG. 1, is adapted to receive a cover, generally indicated 10.

Fixing means such as, for example, complementary screwing means, may be provided between this upper part 9 of the flask and the cover 10.

For this purpose, the upper part of the flask is threaded whereas the corresponding part of the cover 10 is tapped, enabling the cover to be screwed onto the corresponding end of the flask.

The open end of the tube 7 is thus protected.

Moreover, the lower part of the flask comprises a decantation cone, generally indicated 11.

The means, generally indicated 8, for holding the tube 7 in position in the flask are shown in greater detail in FIG. 2.

In fact, these holding means may comprise position-maintaining arms extending between the flask 1 and the tube 7.

In the embodiment illustrated, three position-maintaining arms are shown, arranged substantially 120° apart.

Naturally other configurations may be provided.

One of the arms such as, for example, the arm 12, may be provided with abutment means for enabling a sampling brush to be detached in conventional manner from a manipulating handle thereof in order for the brush to fall into the strainer-forming web of filtering material.

These abutment means are, for example, formed by a recessed portion 13 of the arm.

The arm and the recessed portion may likewise be provided with barbs forming means for combing a sampling brush, in order to cause the elements sampled and held on the brush to fall into the strainer-like filtering means if it is not desired to deposit the brush in the strainer-forming means.

It is then intended that the suspension may be extracted, for example, by an extraction pipette introduced into the tube 7, permitting the retrieval of the different levels of the suspension between the filtering means and the decantation cone.

Naturally, other embodiments may also be envisaged.

Thus, for example, a variant of the flask is shown in FIG. 3.

The flask, generally indicated 1, and its tube, generally indicated 7, can in fact be seen in FIG. 3.

The cover, generally indicated 10, which is adapted to be screwed onto the corresponding end of the flask 1, can also be seen in this drawing.

According to the embodiment shown in FIG. 3, the cover 10 comprises, facing the corresponding end of the tube, at least one piercable and self-sealing region or portion through which the extraction pipette can pass.

In the embodiment illustrated, this cover comprises such a region, generally indicated 10a, provided, for example, in the centre of the cover 10, allowing the pipette or any other extraction means to pass through.

Piercable and self-sealing regions of this type are already known per se in the prior art.

They will not therefore be described in greater detail below.

It will likewise be noted that this region is adapted to come to bear against the corresponding end of the tube 7 during the screwing of the cover onto the remainder of the flask 1, to ensure optimal leaktightness between the tube 7 and the remainder of the flask, thus preventing any contamination.

Naturally, yet further embodiments may be envisaged.

The invention claimed is:

1. A flask for preparing a fixer-based cytological suspension, equipped with means for filtering (4) at least partially immersed in the suspension, wherein the means for filtering (4) are in a form of a web of filtering material forming a strainer, whereof a periphery (5) is fixed to the flask and whereof a centre (6) is connected to a tube (7) that extends towards an opening (2) of the flask, and a plurality of position-maintaining arms (8, 12) extending between the flask (1) and the tube (7) for holding the tube (7) in position in the flask, and is adapted to allow through a pipette for extracting the suspension.

2. The flask according to claim 1, wherein an upper part (9) of the flask is adapted to receive a cover (10).

3. The flask according to claim 2, wherein the cover (10) and the corresponding part (9) of the flask (1) comprise complementary means for screwing.

4. The flask according to claim 2, wherein the cover (10) comprises, facing a corresponding end of the tube (7), at least one piercable and self-sealing portion (10a) through which the extraction pipette can pass, and which is adapted to come to bear against that end of the tube (7) in order to ensure leaktightness between the tube (7) and a remainder of the flask (1).

5. The flask according to claim 1, wherein a lower part of the flask (1) comprises means (11) forming a decantation cone.

6. The flask according to claim 1, wherein one (12) of the arms comprises abutment means (13) for enabling a sampling brush to be detached from a manipulating handle in order for the brush to fall into the strainer.

7. The flask according to claim 1, wherein one of the arms (12) comprises barbs for combing a sampling brush in order to cause elements sampled thereby to fall into the strainer.

8. The flask according to claim 3, wherein the cover (10) comprises, facing a corresponding end of the tube (7), at least one piercable and self-sealing portion (10a) through which the extraction pipette can pass, and which is adapted to come to bear against that end of the tube (7) in order to ensure leaktightness between the tube (7) and a remainder of the flask (1).

9. The flask according to claim 2, wherein a lower part of the flask (1) comprises means (11) forming a decantation cone.

10. The flask according to claim 3, wherein a lower part of the flask (1) comprises means (11) forming a decantation cone.

11. The flask according to claim 4, wherein a lower part of the flask (1) comprises means (11) forming a decantation cone.

12. The flask according to claim 2, wherein a holding arm (12) comprises barbs for combing a sampling brush in order to cause elements sampled thereby to fall into the strainer.

13. The flask according to claim 3, wherein a holding arm (12) comprises barbs for combing a sampling brush in order to cause the elements sampled thereby to fall into the strainer.

14. The flask according to claim 4, wherein a holding arm (12) comprises barbs for combing a sampling brush in order to cause the elements sampled thereby to fall into the strainer.

15. The flask according to claim 5, wherein a holding arm (12) comprises barbs for combing a sampling brush in order to cause the elements sampled thereby to fall into the strainer.

* * * * *